United States Patent [19]
Langenberg et al.

[11] Patent Number: 5,416,010
[45] Date of Patent: May 16, 1995

[54] OLPIDIUM ZOOSPORES AS VECTORS OF RECOMBINANT DNA TO PLANTS

[75] Inventors: Willem G. Langenberg, Martell; Lingyu Zhang, Lincoln, both of Nebr.

[73] Assignee: The United States of America as represented by the Secretary of Agriculture, Washington, D.C.

[21] Appl. No.: 74,902

[22] Filed: Jun. 10, 1993

[51] Int. Cl.$^6$ ............... C12N 15/00; A01H 5/00; A01H 5/10
[52] U.S. Cl. ................ 435/172.3; 435/172.1; 435/320.1; 800/200; 800/250; 800/DIG. 52; 800/DIG. 58; 800/205
[58] Field of Search ............ 800/200, 205, 235, 255, 800/250, DIG. 58, DIG. 52, 55, 56, 57, 58; 424/418; 435/69.1, 171, 172.1, 172.3, 320.1; 935/52, 55, 56

[56] References Cited
PUBLICATIONS

Ingo Potrykus, "Gene Transfer to Cereals: An Assessment," Review in Bio/Technology 8: 535 (Jun. 1990).
W. P. Mowat, "*Olpidium brassicae:* Electrophoretic Mobility of Zoospores Associated with Their Ability to Transmit Tobacco Necrosis Virus," Virology 34: 565 (1968).
J. A. Lesnaw et al., "The Structure of Tobacco Necrosis Virus. II. Terminal Amino Acid Residues of the Protein Subunit," Virology 39: 738 (1969).
L. W. Stobbs et al., "Specificity and Method of Transmission of Cucumber Necrosis Virus by *Olpidium radicale* Zoospores," Canadian Journal of Plant Pathology 4: 134 (1982).
B. Kassanis et al., "The Transmission of Satellite Viruses of Tobacco Necrosis Virus by *Olpidium brassicae*," Journal of General Virology 3: 227 (1968).
Ernest Hiebert et al., "The Assembly in vitro of Some Small Spherical Viruses, Hybrid Viruses, and Other Nucleoproteins," Virology 34: 492 (1968).
D. S. Teakle, "Transmission of Tobacco Necrosis Virus by a Fungus, *Olpidium brassicae*," Virology 18: 224 (1962).
P. R. Fry et al., "Transmission of a Tobacco Necrosis Virus by *Olpidium brassicae*," Virology 30: 517 (1966).
D. S. Teakle, "12. The Effect of Environmental Factors on Fungus-Transmitted Viruses and Their Vectors," In Viruses with Fungal Vectors, pp. 167–179, Assoc. of Applied Biologists, Wellesbourne, Warwick CV9ES, United Kingdom (1988).
French et al. 1986. Science. 231: 1294–1297.
Goodman et al. 1987. Science. 236: 48–54.
Brisson et al. 1984. Nature. 310: 511–514.

*Primary Examiner*—David T. Fox
*Assistant Examiner*—Erich E. Veitenheimer
*Attorney, Agent, or Firm*—M. Howard Silverstein; Curtis P. Ribando; John D. Fado

[57] ABSTRACT

A method is provided for introducing a foreign gene into a plant cell by means of an Olpidium zoospore vector having associated with it a reassembled nucleoprotein complex comprising the foreign gene and reassociated coat protein of a zoospore-transmissable virus. The plant cell is contacted with the zoospore under conditions suitable for transmission of the nucleoprotein complex into the cell. The method can be conducted under nonsterile conditions, is applicable to all nucleic acids regardless of size, and is useful for introducing foreign genes into cells of both monocots and dicots.

6 Claims, 2 Drawing Sheets

OLPIDIUM ZOOSPORES AS VECTORS OF RECOMBINANT DNA TO PLANTS

BACKGROUND OF THE INVENTION

1. Field of the Invention

Interest in transformation of crop and horticultural plants with added desirable agronomic traits is very high. Powerful new techniques for gene transfer recently have been developed for moving single genes and whole blocks of genes from one plant to another and even for moving genes from non-plants into plants. These new techniques are useful for generating specific plant genotypes and for the long term achievement of greater plant diversity through gene recombination. This invention relates to a novel method for introducing foreign genes into both monocotyledonous and dicotyledonous plants, thereby circumventing many of the limitations associated with the present-day technology in this field.

2. Description of the Prior Art

Several methods have been explored for introducing nucleic acid into a variety of cell types with the hope of developing a successful technique for the transformation of eukaryotic cells of plants and animals. A review of these methods is given by Potrykus [Biotechnology 8:535-541 (1990)].

Early approaches to transforming plants and animals focused on protoplast fusion [W. Schaffner, Proceedings National Academy Science U.S.A. 77:2163-2167 (1980); M. Rassoulzadegan et al., Nature 295:257-259 (1982)] and calcium phosphate coprecipitation with DNA or recombinant bacteriophage [F. L. Graham et al., Virology 52:456-467 (1973); M. Ishiura et al., Molecular Cell Biology 2:607-616 (1982)]. More recently, electroporation has been successful in introducing DNA into plant protoplasts [M. Fromm et al., Proceedings National Academy Science U.S.A. 82:5824-5828 (1985); M. Fromm et al., Nature 319:791-793 (1986)], fibroblasts [H. Liang et al., Biotechniques 6:550-558 (1988)], and mammalian red blood cells [T. Y. Tsong et al., Bibliographical Haematology 51:108-114 (1985); G. Chu et al., Nuclear Acids Research 15:1311-1326 (1987)].

Another approach which has been thoroughly investigated involves the use of Agrobacterium tumefaciens, and its tumor-inducing (Ti) plasmid. The use of vital vectors has also been considered [N. Brisson et al., Nature 310:511-514 (1984)].

Physical methods of introducing nucleic acid into cells include biolistic delivery IT. M. Klein et al., Bio/-Technology 6:559-536 (1988); D. E. McCabe et al., Bio/-Technology 6:923-926 (1988); and P. Christou et al., Plant Physiology 87:671-674 (1988)], Microinjection [G. Neuhaus et al., Theoretical Applied Genetics 75:30-36 (1987)], and infusion of cells physically disrupted with glass beads [Constanzo et al., Genetics 120:667-670 (1988)] or mineral fibers [Appel et al., Proc. Natl. Acad. Sci. U.S.A. 85:7670-7674 (1988); Kaeppler et al., Plant Cell Reports 9:415-418 (1990)].

There are several drawbacks to the aforementioned methods of DNA transformation in plants. Any of the techniques which uses or treats protoplasts is limited by the fact that protoplasts from many plant species are recalcitrant to regeneration into mature genetically stable plants. Accordingly, many of the most important economic crop plants have never been regenerated from protoplasts. In most cases where regeneration has been achieved, the production of plants from transformed protoplasts involves lengthy sterile culture and regeneration procedures.

The success of the electroporation method is dependent, in part, on optimizing parameters relative to the membrane, the DNA, and the electric field. Evidence for the success of transformation after electroporation has been measured by incorporation of radioactively labeled DNA [Tsong et al., supra], transient gene expression [H. Potter et al., Proceedings National Academy Science U.S.A. 81:7161-7165 (1984); O. Smithies et al., Nature 317:230-234 (1985)], and the formation of stable transformants [C. D. Riggs et al., Proceedings National Academy Science U.S.A. 83:5602-5606 (1986); H. Stopper et al., Z. Naturforsch. 40:929-932 (1985)]. Application of electroporation to cells and tissues has not been successful for generating transgenie clones, particularly in plants. Gene transfer by electroporation of protoplasts has met with some success, but the aforementioned problems of plant regeneration still exist.

Transformation of the most important crop plants, such as the cereals and legumes, has proven difficult with Agrobacterium. Agrobacterium has been shown to attach to wheat callus cells but no stable transformation was obtained [P.J. Dale et al., John Innes Institute Annual Report (1988); K. Dehesh et al. Science 250:1397 (1990)]. The number of plant species that are infected by this system is extremely limited, and other bacterial vectors are not currently available. Plant viruses are not known to integrate into the host genome and therefore show limited potential as vectors for stable transformation.

At present, the physical approaches seem to hold the most promise for genetic modification of cereals. However, the frequency of transient and integrative events with these techniques tends to be low. In plants, there is considerable difficulty in targeting cells that are competent for regeneration and/or integrative transformation. The meristem in cereals is well-protected, and it is unsettled whether any of the meristematic cells are competent for integrative transformation.

SUMMARY OF THE INVENTION

We have now developed a method for introducing a desired nucleic acid into a plant cell via an Olpidium zoospore vector. The zoospore is associated with a reassembled virus nucleoprotein complex comprising:

(1) the desired gene as the core of the complex;
(2) and a protein coat.

The coat is reassociated protein obtained from a virus which is normally transmitted by the Olpidium zoospores. Alternatively, the protein originates from a virus which does not normally associate with Olpidium, but which has been modified to express a coat protein having the zoospore recognition site of a zoospore-transmissible virus. We believe that this method is applicable to virtually all types of nucleic acid, regardless of size or function. The ubiquitous host range of Olpidium permits application of the method to virtually all plant species.

In accordance with this discovery, it is an object of the invention to provide a novel method for introducing foreign genes into both monocotyledonous and dicotyledonous plants under nonsterile conditions. Any plasmid, or modified plant viral DNA, capable of being expressed in plant cells can be introduced with the method.

Another object of the invention is to successfully package a gene of interest i the reassembled coat protein of an Olpidium zoospore-transmissible virus.

It is also an object of the invention to demonstrate that a nucleoprotein complex comprising reassembled coat protein of an Olpidium zoospore-transmissible virus will associate with Olpidium zoospores regardless of the morphology of the complex.

A further object of the invention is to provide a potential route for the stable transformation of both monocotyledonous and dicotyledonous plants.

Other objects and advantages of the invention will become readily apparent from the ensuing description.

DETAILED DESCRIPTION OF THE INVENTION

Figure 1:
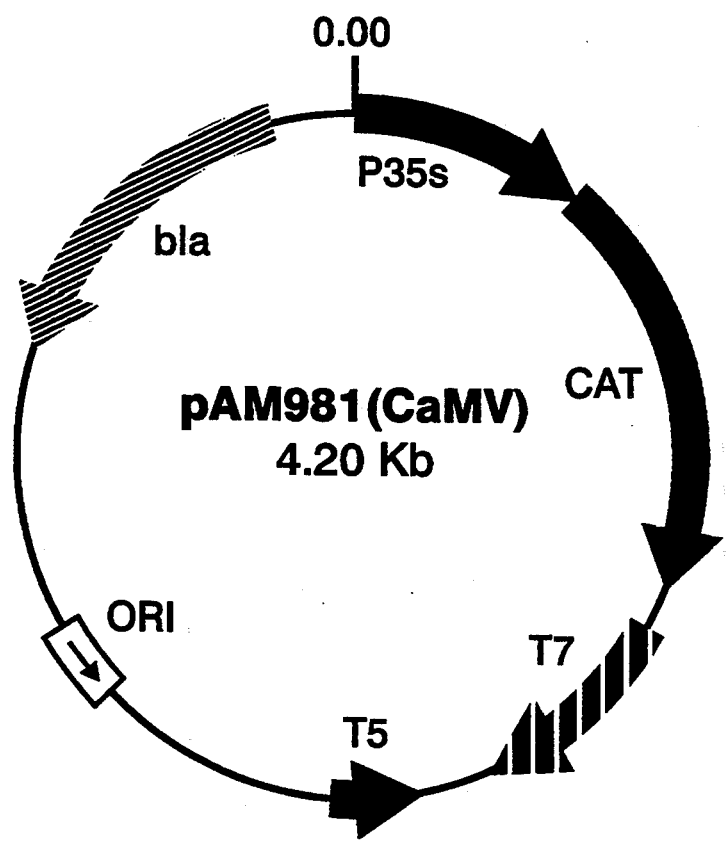
FIG. 1 is a schematic representation of the plasmid pAM981(CaMV), which was encapsulated and transferred to wheat by the method of the invention.
Figure 2:
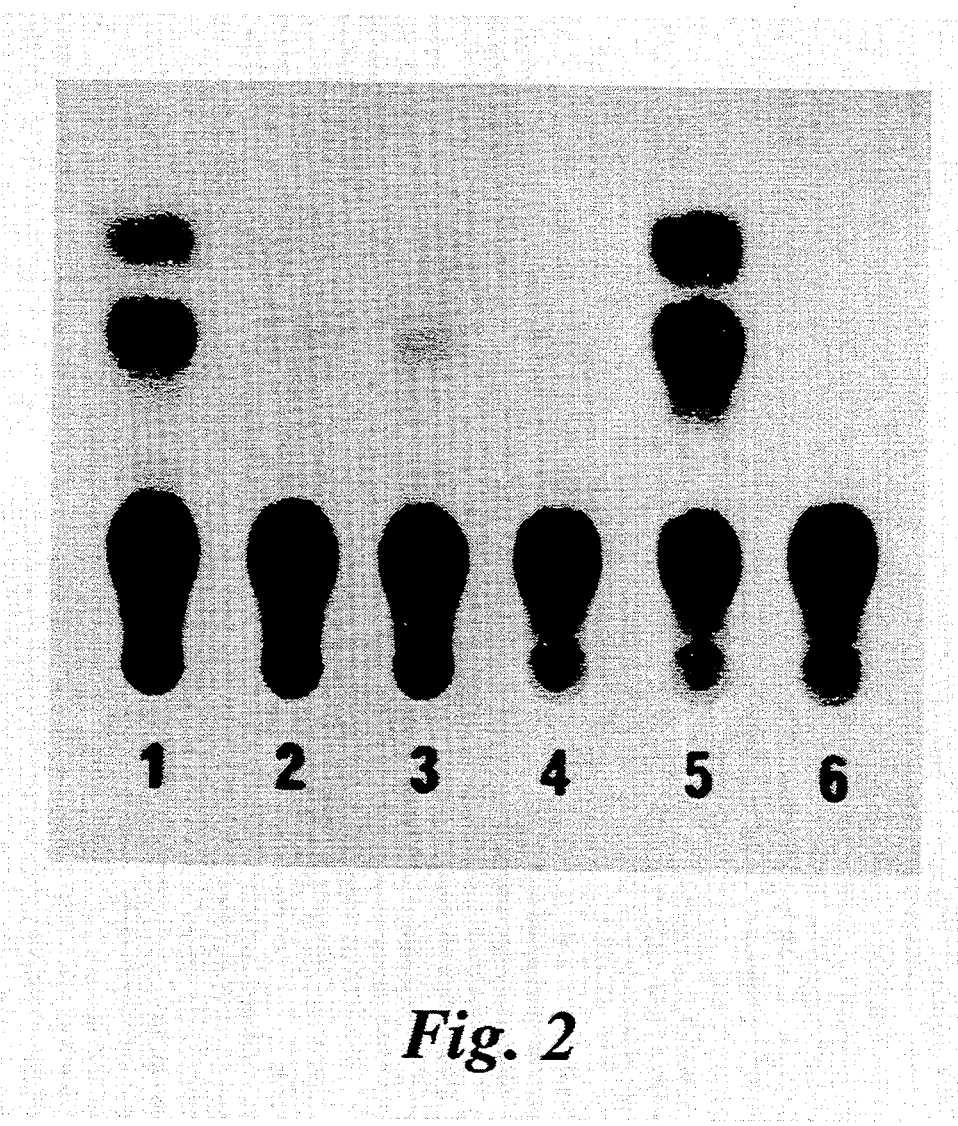
FIG. 2 is an autoradiograph of a series of assays for CATase activity in variously-treated wheat roots.

For purposes of the ensuing discussion, the expressions "gene of interest", "foreign gene", "foreign nucleic acid" etc. are used in reference to any DNA or RNA oligonucleotide which is desireably introduced into a target cell. Typically, the oligonucleotide is not native to either the plant cell or the genome of the virus used as the source of the nucleoprotein complex vectored by the Olpidium zoospores.

The process of the invention is believed to be applicable to all species of plants, whether monocotyledonous or dicotyledonous, that are susceptible to infection by Olpidium. Of particular interest are agriculturally-important plants, such as field crops, horticultural crops, and orchard crops. The method of the invention is especially advantageously applied to the gramineous crops, such as wheat, corn, sorghum, barley, rye, rice, triticale and the like, and also the legumes, such as soybeans, alfalfa, and stringbeans. The widespread host range of Olpidium extends its utility to virtually all plants of interest.

Olpidium is a ubiquitous soil-borne fungus which infects plants through the roots. Particularly susceptible to adsorption and penetration of the fungal zoospores are root cells in the zone just behind the meristematic region of the root tip. Penetration takes place 2–4 hours after intial contact. The fungal body responsible for plant infection is the zoospore, which may eventually be absorbed by the root cells when in a motile stage and become encysted on the plant roots.

Species of Olpidium are, in turn, vectors of specific viruses, many of which are associated with agronomically important viral diseases in crop and horticultural plants. For example, O. brassicae is the vector of tobacco necrosis virus (TNV) and O. radicale vectors cucumber necrosis virus (CNV). These viruses associate with the zoospores and are vectored into the Olpidium host plant cell at the time of infection by the fungal body. It is contemplated that the method of this invention can be carried out using any compatible combination of host plant, Olpidium species, and virus.

Stobbs et al. [Canadian Journal of Plant Pathology 4:134–142 (1982)] report that CNV acquisition by O. radicale zoospores appears to be associated with the protein coat of the virus. We have found through propagation by manually inoculating plants with TNV that the virus may mutate to a form which is not recognized by O. brassicae zoospores. This suggests that the recognition site on the coat protein of the virus is relatively small and the genomic region encoding for this site could be inserted into the genome of other viruses, such as tobacco mosaic virus. In this way the specificity of viruses for particular Olpidium species could be circumvented and the useful range of Olpidium species for vectoring a foreign gene into a plant cell can be extended.

The gene of interest selected for introduction into the plant cell may be virtually any DNA or RNA oligonucleotide without regard to the size, type or strandedness of the foreign nucleic acid relative to the native form of the original virus. It is not necessary for the reassembled nucleoprotein complex to have the same morphology as the original virions in order for the recognition sites on the protein coat to associate with the receptors on the Olpidium zoospores. Therefore, in situations where the nuclear material presented for reassembly is significantly larger than the viral genome, the protein subunits will coat the strands of nuclear material without packaging it into the same geometric structure of the parent virus. For example, the nucleoprotein complex formed by TNV capsid protein and herring sperm DNA larger than about 10 kb has a rope-like appearance. If the nucleic acid is small enough, a "pseudovirion" will form in which the capsid is morphologically indistinguishable from that of the parent virion. It is not uncommon for a small percentage of the reassembled capsids to be devoid of nuclear material. These can readily be distinguished by conventional negative staining techniques and electron microscopy of preparations.

In the case of intact TNV and many other RNA viruses, the RNA is simply balled up inside the icosohedral capsid. The capsid protein forms a shell around the RNA and the subunits are configured in a manner which orients the positively charged amino acids toward the inside of the capsid to counteract the negative charges of the RNA. In the reassembled nucleoprotein complexes, the protein and core nucleic acid should be similarly arranged, even when the size of the nucleic acid precludes the formation of identifiable pseudovirions.

The gene of interest would normally be inserted with appropriate control sequences into a plasmid or the like, and expanded in a cloning system by methods well known in the art. The expanded gene would then be combined with dissociated viral coat protein for subsequent encapsidation.

There are several reports in the literature of successful in vitro dissociation and/or reassociation of plant viruses. Exemplary reports of such with icosahedral plant RNA viruses include: J. B. Bancroft et al. [Virology 39:924–930 (1969)]; B. Chen et al. [J. General Virology 71:939–944 (1990)]; E. Hiebert et al. [Virology 34:492–508 (1968)]; C. Hsu et al. [Virology 69:587–595 (1976)]; C. Hsu et al. [Virology 81:471–475 (1977)]; J. Kaper [Virology 37:134–139 (1969)]; J. Kaper ["Controlled Disruption and Stabilizing Interactions of Turnip Yellow Mosaic Virus," In The Ghemical Basis of Virus Structure, Dissociation and Reassembly, p. 276, North-Holland Publishing Company (1975)]; J. M. Kaper et al. [J. Molecular Biology 56:277–294 (1971)]; D. McCarthy et al. [J. General Virology 46:391–404 (1980)]; O. P. Sehgal et al. [Virology 77:1–11 (1977)]; O. P. Sehgal [Phogopathology 63:629–633 (1973)]; P. K. Sorger et al. [J. Molecular Biology 191:639–658 (1986)]; J. H.

Tremaine et al. [*Canadian Journal of Botany* 55:2274-2277 (1977)].

The conditions for dissociation and reassociation suggest that there are at least two main types of interaction that are involved in virion stability of some viruses: namely, protein-protein and protein-RNA JR. E. F. Matthews "Plant Virology," 3rd Edition, Academic Press, Inc. San Diego, Calif. (1991); M. G. Rossmann et al., *J. Molecular Biology* 166:37-83 (1983)]. Agents which interfere with these interactions are referred to herein as "destabilizing agents" or "disassembly agents" and are inclusive of any cations, anions, salts, chelating agents, etc. which have the effect of dissociating the virus under appropriate effective conditions of agent concentration, temperature, pH, solvent type, etc. Once a suitable destabilizing agent is determined for a given virus, then the optimum conditions for effecting dissociation can be readily determined by the person of ordinary skill in the art.

We have discovered that TNV can be dissociated with dilute solutions of ethylenediaminetetraacetic acid (EDTA) or phosphotungstic acid (PTA) at temperatures in the range of 5°-25° C. in about 30 minutes. For example, a 2% solution of PTA at pH 7.0 dissociates most TNV particles. At pH 1.8, 2% PTA causes a release of TNV RNA from the capsid while leaving the capsid almost intact. Addition of KCl will result in dissociation of the capsid into smaller units. At pH 7.0, 2% PTA partially disrupts the TNV virions, yielding broken capsids. Likewise, incubation of TNV with 15 mM EDTA at pH 8 for one hour results in dissociation of the virions.

After dissociation, it is usually desirable to isolate the protein subunits from the viral nucleic acid. Residual RNA associated with the disassembled protein can be nuclease-degraded, and then the protein can be separated out by dialysis or other suitable method as known in the art. For instance, in the case of TNV disassembled with EDTA, it is necessary to treat the material with RNase in order to free the protein from adhering residual RNA. The isolated protein is thereby made available for reassembly around the foreign nucleic acid without interference from the native RNA. The isolation step also insures that virulent virus is not transmitted by the zoospores. EDTA or other salts are removed by dialysis, such as with dialysis tubing having a molecular weight cutoff at 6,000–8,000.

The virus is reassembled into a nucleoprotein complex by subjecting a solution of the isolated viral protein and the foreign nucleic acid to a dialysis treatment by which divalent ions are allowed to diffuse into the mixture. Preferred divalent ions include $Mg^{++}$ and $Ca^{++}$.

As with virus dissociation, the conditions for reassembly are specific to the particular parent virus. Also, the conditions of disassembly and isolation, together with the nature of the foreign nucleic acid, may influence the structure of the reassembled particles. We have observed that reassembly of dissociated TNV (from 2% PTA treatment) with dsRNA formed particles which had the same size as the native virus (28 nm). These particles were penetrated by uranyl acetate as a negative stain, indicating that they were different in structure from native virions. In contrast, reassembly of the same dissociated Virus material with ssDNA or dsDNA formed smaller particles with a diameter of 24 nm. Reassembled TNV (from 15 mM EDTA) with dsRNA formed spherical particles which were about 46 nm in diameter. Particles averaging about 90 nm in diameter resulted from the EDTA-dissociated virus reassembled with dsDNA. Nuclease resistance of the nucleoprotein complex verifies that the reassembled protein subunits do, indeed, encapsidate the foreign nucleic acid.

The particles of encapsidated foreign nucleic acid are associated with Olpidium zoospores by combining these materials in an aqueous medium and incubating for a period of about 20–40 min at 15°–20° C. The resulting dispersion of zoospores and associated pseudovirions is suitable for use as is.

For the purpose of achieving transient expression of the foreign gene in a target plant, the plant's roots are exposed to the zoospores carrying the encapsidated gene. This is easily carried out by inoculation of the roots in a dispersion of the zoospores at a temperature of about 15°–20° C., for a period of at least 2 hrs. At the conclusion of the incubation, the Olpidium zoospores are killed, such as by placing the roots in a water bath at 40° C. for 10 min. Successful introduction of the foreign gene into the plant cells is established by appropriate assay for the expression products of either the gene itself or a marker gene.

Stable transformation would be accomplished by transfection of embryonic cells with the pseudovirions. Monocots form a nodal plate approximately 2.5 cm (1") below the soil surface. This tissue is rich in embryonic cells from which tillers and roots arise. The nodal plate would be excised from the seedling and incubated with the Olpidium zoospores and associated pseudovirions described above in regard to the treatment of roots. After heat-killing the zoospores, the plate is inoculated on a root- and shoot-promoting medium with appropriate antibiotics and a fungicide to promote plant development. Candidate transformants are assayed for expression of the foreign gene or a marker gene as previously described.

It is envisioned that this invention would be useful for introducing into plants genes related to desireable agronomic traits, such as: enhanced growth; improved seed, fruit or vegetable production, disease and insect resistance, maturation control, constituent alteration, etc.

The following examples are intended only to further illustrate the invention and are not intended to limit the scope of the invention which is defined by the claims.

EXAMPLE 1

Isolation of TNV Protein

A Nebraska isolate of tobacco necrosis virus, hereafter referred to as TNV-NE, was maintained on leaves of cowpea [*Vigna sinensis* (Thorner) Savi cv Pink eye]. Five hundred g frozen primary leaves of cowpea containing numerous local lesions were ground in 1,500 ml of cold 0.1M ammonium citrate, pH 5.2, containing 10 mM EDTA and 1% Na dithionite. Juice from the grind was clarified by low speed centrifugation (16,000×g, 10,000 RPM for 20 min in a GSA rotor, Sorvall RC-2B centrifuge). Virus was purified by one high speed and one low speed cycle of centrifugation followed by banding in 40% cesium chloride, and finally dialyzed free of CsCl against several changes of glass distilled water using 12,000–14,000 MW cutoff dialysis bags (Spectrapor, Los Angeles, Calif.). This purification process appeared to remove most contaminating satellite TNV (STNV) as evidenced by SDS-PAGE. STNV shares a common host range with many isolates of TNV and is also transmitted by Olpidium zoospores.

The purified virions were disrupted as follows. TNV (0.3–0.7 mg/ml) [A260 of 5.5=1 mg TNV/ml] was dissolved in 15 mM EDTA and incubated at 5° C. for 1 hour to disrupt the virions. In order to dissociate the RNA from the protein, KCl was added to a final concentration of 0.4 M. The solution was kept for another hour at 5° C. at which time RNase was added at a level of 1 g/ml. Residual RNA associated with the protein was removed by RNase digestion at 20°–25° C. for 1 hr. The purified TNV protein was recovered for use in encapsidating the plasmid pAM 981 as described, below.

Construction of Plasmid pAM981

The plasmid pAM 981 (essentially equivalent to precursor pAM325) was constructed by ligating the SalI fragment containing cauliflower mosaic virus 35S promoter, the chloramphenicol acetyl transferase (CAT) reporter gene and the T7 and T5 transcription terminators from pGA 663 [Mitra et al., Plant Molecular Biology 12:169–179 (1989)] to the SalI site of pUC 19. The resulting 4.2 kb construct is shown in FIG. 1.

Encapsidation

The plasmid pAM 981 and the purified TNV protein were combined in a weight ratio of 2:1. The mixture was dialyzed against glass distilled water containing 10 mM NaCl, 10 mM $MgCl_2$ and 30 mM $CaCl_2$ overnight (18 hrs) at 5° C. resulting in the formation of 40×75 nm particles, or pseudovirions. These particles were considerably larger than the TNV icosahedron of 25–30 nm.

For verification that plasmid DNA was encapsidated, particles were first centrifuged twice through a 20% (w/v in glass distilled water) sucrose cushion in a Beckman SW55 rotor at 45,000 RPM (246,000×g) for 1.5 hr. The final pellet was dissolved in glass distilled water, and the supernatant from the last centrifugation was saved as a negative control (to show that no free DNA was present in the supernatant). A 10 g sample of plasmid DNA served as a positive control. DNase II (0.4 g, Sigma D-8764) was added to 100 μl of the particle suspension and the plasmid solution each dissolved in 0.83 mM $Mg^{2+}$, pH 4.6. The two solutions were then incubated at 37° C. for 15 min to allow for optimal enzymes digestion. At the conclusion of the digestion, DNA was obtained by phenol extraction. All DNA samples were digested with HindIII before loading on a 1% agarose gel containing 1 g/ml ethidium bromide as a stain. The resulting autoradiograph (not shown) was characterized by the following features. Lane 1, DNA size markers comprising a commercial preparation of lambda DNA digest with Hind III ranging in size from 23130 to 561 bp; lane 2, digested unencapsidated plasmid pAM 981 DNA after DNAse treatment; lane 3, no bands, indicating no DNA was present in the last supernatant of a pseudovirion preparation after three high speed centrifugations of pseudovirions through a 20% sucrose cushion at 45,000 RPM (246,000×g) in a Beckman SW 55 rotor, for 1.5 hrs; lane 4, a single bright band at 4.2 kb, indicating untreated unencapsidated plasmid DNA; lane 5, representing DNA phenol-extracted from pseudovirions that had been treated with DNase, wherein a single band at 4.2 kb indicated intact plasmid DNA; lane 6, plasmid DNA phenol-extracted from untreated pseudovirions again having a single band at 4.2 kb indicating intact plasmid DNA; and lane 7, DNA size standards.

Olpidium Culture

A Nebraska isolate of Olpidium brassicae (Wor.) Dang was maintained in roots of lettuce (Lacuca sativa L. cv Early Butterhead) or wheat (Triticum aestivum L. cv Vona) in growth chambers set at 17° C. with a 12 hr light/dark cycle. Plants were grown in plastic pots (6×6 cm) in coarse sand and watered as needed to maintain turgor.

Incubation of Zoospores with Pseudovirions

Water was withheld from 4–8 wheat plants that had been rootinoculated 3–6 weeks earlier for 12–24 hrs with a suspension of the Olpidium zoospores described above. Plants were pulled from the small plastic pots and sand rapidly rinsed from the roots with running cold (−13° C.) tapwater. Roots were placed in a minimal amount of distilled water. Zoospores were released from zoosporangia within 15 min. Water was decanted in 50 ml centrifuge tubes and the newly released zoospores concentrated by a 5-min 5,000 RPM (4,000×g) centrifugation in a swinging bucket rotor (Sorvall HB4) in a refrigerated (5°–10° C.) Sorvall RC-2B centrifuge. At the conclusion of the centrifugation, water was aspirated to approximately the 5 ml level, the centrifuge tube gently swirled and approximately 300 g of the TNV nucleoprotein particles prepared, above, added. The zoospore and particle solution was incubated at 20° C. for 30 min.

Inoculation of Wheat Plants

Two-day old wheat seedlings were placed in the zoospore-nucleoprotein particle solution for a period of 4 hr. in the dark at a temperature of 20° C. Four hours later, bare roots were placed in a 40° C. water bath for 10 min to kill the zoospores, including those that had already penetrated the root epidermal cells. No, or very little, infection by Olpidium occurred in heat-treated controls. At the completion of the heat treatment, wheat seedlings were grown in coarse sand for 60–70 hrs at 20°–25° C. under continuous light. Plants were watered as needed with tap water.

After about 2 days of growth, the wheat root cells were assayed for CAT expression. The roots (now 3–6 cm in length) were washed free of sand and excised from the plant. Both the root tips (1–1.5 cm) and the rest of the root were separately processed for CATase activity as described by C. M. Gorman et al. [*Molecular Cell Biology* 2:1044–1051 (1982)]. The results of the assay are shown in FIG. 2. Lane 1 shows the CATase activity of root material exposed to zoospores carrying particles encapsidating pAM 981. Lane 2 represents roots exposed to zoospores and unencapsidated plasmids and having no significant CAT expression. In lane 3, roots exposed to unencapsidated plasmids only showed no significant CATase activity. In lane 4, roots and zoospores only also had no significant CATase activity. Lane 5 is the CAT enzyme positive control and lane 6 is the negative control with no CAT enzyme. Thus, only for that treatment where wheat seedlings received zoospores and nucleoprotein particles was CATase activity present to a significant degree. The experiment presented in this Example was repeated two more times as described, each time with the same result.

In a series of control experiments, celite-dusted leaves of cowpea and wheat seedlings and wheat roots were manually inoculated with particles carrying the pAM 981 plasmid dissolved in glass distilled water. Leaf and root tissues were assayed for CATase activity 2.5–3 days later. No CATase activity was found in any of the manually inoculated tissues. This established that it was not possible to introduce nucleoprotein particles into cells by manual inoculation (negative CATase assay results not shown).

EXAMPLE 2

Various conditions of virus disassembly were tested against the Nebraska isolate of TNV. SDS-PAGE gel with silver staining revealed only one band of about 30 kDa, representing the TNV capsid protein. This indicated that no significant level of STNV was present in the TNV preparation. The putative destabilizing or virion disassembling solutions were tested as follows:

A. 1M NaCl, 20 mM Tris, 1 mM DTT, pH 7.4; at −4°–5° C.
B. 1.5M KCl; at 30° C.
C. 2M LiCl; at −20° C. or −80° C.
D. 1M $CaCl_2$; at −4°–5° C.
E. 66% formic acid; at 37° C.
F. 1N HCl; at room temperature
G. 50 mM glycine, pH 9.0; at −4°–5° C.
I. 2% phosphotungstic acid (PTA), pH 1.8; at room temperature 2% PTA, pH 7.0; at room temperature
J. 0.1M Tris, 10 mM EDTA, 0.4 M KCl, pH 8.0; at −4°–5° C.
K. 15mM EDTA, pH 8.0; at −4°–5° C.

After appropriate incubation time, samples were negatively stained with 2% (w/v) uranyl acetate and examined in a ZEISS EM10A transmission electron microscope (TEM) to assess dissociation. Agarose gel electrophoresis was also used to evaluate the dissociation results. In this method, the samples were loaded onto 1% agarose gels in 45 mM Tris-borate, 1 mM EDTA, pH 8.7 (TBE) buffer containing ethidium bromide (1 g/ml). One mM EDTA sufficiently destabilizes the virions to cause swelling. This in turn allows ethidium bromide penetration and reaction with viral RNA so that it can be visualized with UV light. After photographing, the gel was stained with "Coomassie Brilliant Blue R" (Sigma) and destrained. The resultant gel was dried and rephotographed.

Dissassembly solutions A, B, G, D, E, F, and G failed to disrupt TNVNE virions. Formulation F caused crystallization of TNVNE virions.

Solution H at 25° C. disrupted the virions of TNV-NE. This formulation caused a release of TNV RNA from the capsid, leaving the capsid almost intact but swollen. The released RNA was partially degraded by contaminating RNase in the virus preparation. Addition of KCl either at the same time with the PTA or one hour after incubation of the virus with PTA at room temperature resulted in the dissociation of the capsid into smaller units than with PTA alone. When KCL was added at the same time with PTA, the RNA seemed to be free from the coat protein and to remain undegraded by contaminating RNase.

Solution I at 25° C. partially disrupted virions.
Solution J at 5° C. partially disrupted virions.
Solution K incubated with virus for 1 hr at 5° C. dissociated TNV-NE particles. However, addition of 0.4M KCl at the same time as the EDTA served to inhibit the disassembly process.

EXAMPLE 3

The dissociated TNV-NE virus solutions obtained from Example 2 were used for reassembly with different types of nucleic acid, including:

dsRNA: artificial dsRNA poly(I)/(C), (polyinosinic-polycytidylic acid, with minimum molecular weight of 100,000, about 300 bp, Sigma).
ssDNA: circular, produced from phagemid pBluescript KS(+) with insert (about 4,000 nt); and
dsDNA: supercoiled plasmid pCAMV (4100 bp), or linear phagemid pBluescript KS(+) without insert (3200 bp).

All dialysis steps were performed in SPECTRAPOR membrane tubing with molecular weight cutoff of 6,000–8,000. TEM and a DNase sensitivity test were used to examine the reassembly results.

The nucleic acid was added to the dissociated virus solutions from 2% PTA (Solutions H & I) and dialyzed against running cold (−13° C.) tap water overnight at room temperature or dialyzed against a reassembly solution containing 10 mM NaCl, 10 mM $MgCl_2$, and 30 mM $CaCl_2$ overnight at 5° C.

A DNase sensitivity test was applied to the reassembled particles of dissociated virus protein with dsDNA to investigate nuclease-resistance of the particles (nucleoprotein complexes). The reassembled particles from 2% PTA dissociated virus with dsDNA and control dsDNAs were digested with DNase II (0.1 g/l) under optimal conditions as recommended by the manufacturer (0.83 mM $Mg^{2+}$, pH 4.6 and 25° C. for 1 hr). DNA was then obtained by phenol extraction and loaded on a 1% agarose gel containing 1 g/ml ethidium bromide as a stain.

Reassembly of the PTA-dissociated virus with dsRNA, formed particles which had the same size as the native virus (28 nm). These particles were penetrated by uranyl acetate as the negative stain. This indicates that the particles may be unstable and different in structure from native virions. Reassembly of the dissociated virus with ssDNA or dsDNA formed smaller particles with a diameter of 24 nm.

The reassembled particles from PTA-dissociated proteins with dsDNA were nuclease-resistant in assays against both DNase II and DNase II plus RNase.

EXAMPLE 4

The reassembly procedure of Example 3 was repeated except that some of the reassembly conditions were varied. When 50 mM $CaCl_2$ was substituted for 30 mM $CaCl_2$ in reassembly solution for EDTA-KCl-dissociated virus, only a few large particles or partial particles formed compared to the native TNV virions. However, after a longer dialysis of 42 hrs in 15 or 50 mM $CaCl_2$ (other conditions being the same) spherical particles with diameters of 43 nm and 37 nm were formed. No other morphological differences were observed except for a difference in size.

After overnight dialysis in a reassembly solution containing 10 mM NaCl and 30 mM $CaCl_2$ (no $MgCl_2$ added), mixtures of the dissociated protein solution with dsRNA or dsDNA formed irregularly shaped particles.

Two other reassembly solutions were evaluated:
(1) 5 mM NACl, 5 mM $MgCl_2$, and 15 mM $CaCl_2$; and
(2) 20 mM NaCl, 20 mM $MgCl_2$, and 60 mM $CaCl_2$.
Particles were not efficiently formed using either one of these solutions.

Reassembly of the dissociated protein solution with added nucleic acid after 15 mM EDTA treatment failed to form particles when no KCl and RNase were added to the dissociated protein solution.

EXAMPLE 5

Stable transformation of monocotyledonous plants, as exemplified by wheat, may be carried out as follows: Pseudovirions containing pAM 981 are prepared and associated with Olpidium brassicae zoospores as described in Example 1. Surface-sterilized wheat kernels are planted approximately 7.5 cm (3") below the surface in sterile vermiculite. Nine to 14 days after germination the nodal plate is developed and clearly visible to the naked eye. Excised nodal plates are submerged in a 20 μl droplet containing the Olpidium zoospores and associated pseudovirions and several antibacterial agents. After 2-4 hrs the nodal plates are washed in sterile water containing antibacterial agents and the fungicide metaxyl. This fungicide is active against lower fungi which may also be present in the Olpidium zoospore-virus mixture. After entry and delivery of the plasmid into the embryonic cells of the nodal plate, the zoospores are heat-killed by the procedure of Example 1. Thereafter, the nodal plate is placed on root- and shoot-promoting medium to promote plant development. Individual plants are allowed to go to seed. First generation progeny are grown out and assayed for the presence of CAT to verify stable transformation. This process would be applicable to any plant or foreign gene.

It is understood that the foregoing detailed description is given merely by way of illustration and that modification and variations may be made therein without departing from the spirit and scope of the invention.

We claim:

1. A method for introducing nucleic acid into a gramineous plant cell comprising:
    (a) contacting said cell with an *Olpidium brassicae* zoospore, wherein said zoospore is associated with a reassembled nucleoprotein complex comprising said nucleic acid and reassociated coat protein of tobacco necrosis virus, wherein said contacting is under conditions suitable for transmission of the nucleoprotein complex into the cell and wherein at least a portion of said nucleic acid is not native to said virus; and
    (b) subjecting said cell to conditions whereby said zoospore is inactivated.

2. The method of claim 1 wherein said nucleic acid is plasmid DNA.

3. A method for introducing foreign nucleic acid into a gramineous plant comprising:
    (a) contacting root cells of said plant with an *Olpidium brassicae* zoospore, wherein said zoospore is associated with a reassembled nucleoprotein complex comprising said nucleic acid and reassociated coat protein of tobacco necrosis virus, wherein said contacting is under conditions suitable for transmission of the nucleoprotein complex into the cells and wherein at least a portion of said nucleic acid is not native to said virus; and
    (b) subjecting said root cells to conditions whereby said zoospore is inactivated.

4. The method of claim 3 wherein said nucleic acid is plasmid DNA.

5. A vector for introducing nucleic acid into a plant cell comprising an *Olpidium brassicae* zoospore associated with a reassembled nucleoprotein complex comprising said nucleic acid and reassociated coat protein of tobacco necrosis virus, wherein said nucleic acid comprises nucleic acid which is not native to the virus.

6. The vector of claim 5 wherein said nucleic acid is plasmid DNA.

* * * * *